United States Patent [19]
Faulks et al.

[11] Patent Number: 5,931,826
[45] Date of Patent: Aug. 3, 1999

[54] ABSORBENT ARTICLE WITH VOID VOLUME CONTAINMENT FLAPS

[75] Inventors: Michael John Faulks, Neenah; Bruce Michael Siebers, Appleton; Jody Dorothy Suprise, Neenah, all of Wis.

[73] Assignee: Kimberly-Clark Worldwide, Inc., Neenah, Wis.

[21] Appl. No.: 08/935,763

[22] Filed: Sep. 23, 1997

Related U.S. Application Data

[63] Continuation of application No. 08/570,056, Dec. 11, 1995, abandoned.

[51] Int. Cl.⁶ .............................. A61F 13/15; A61F 13/20
[52] U.S. Cl. ........................................................ 604/385.2
[58] Field of Search ........................... 604/385.2, 385.1, 604/383, 378

Primary Examiner—John G. Weiss
Assistant Examiner—Ki Yong O
Attorney, Agent, or Firm—Thomas D. Wilhelm; Brian R. Tumm

[57] ABSTRACT

An absorbent article includes an absorbent core positioned between a bodyside liner and an outer cover. Containment flaps are inwardly folded to form containment reservoirs which inhibit exudates from leaking through or out of the absorbent article. The containment flaps include flap elastics which form surface contact with the user's body. The containment flaps are generally spaced outwardly from the absorbent core to increase the capacity of the reservoirs. In one embodiment, the unfolded containment flaps have a width greater than the crotch side width from the absorbent core to an outer edge of the absorbent article. This arrangement also allows the absorbent article to contain a sudden increase in exudates.

38 Claims, 7 Drawing Sheets

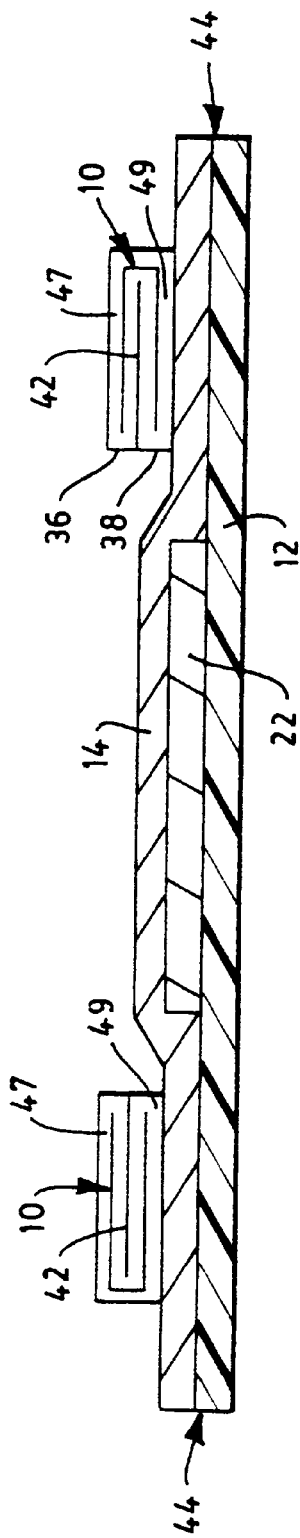
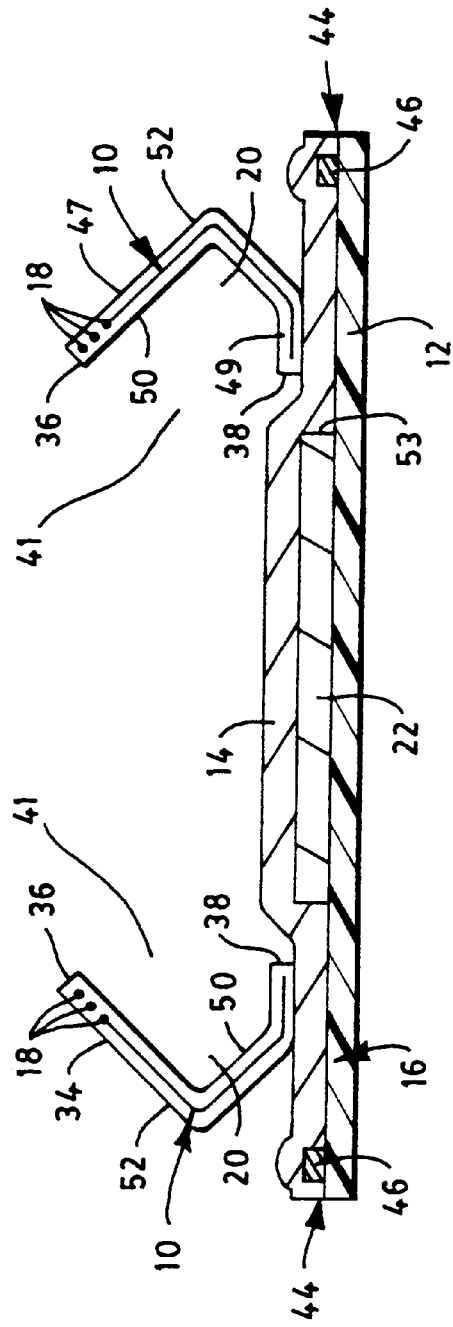

ABSORBENT ARTICLE WITH VOID VOLUME CONTAINMENT FLAPS

This is a Continuation of application Ser. No. 08/570,056 filed Dec. 11, 1995 now abandoned.

BACKGROUND OF THE INVENTION

1. Technical Field

The present invention relates to an absorbent article for containing body exudates. Such absorbent articles may have containment flaps to help contain fecal material, urine or other exudates.

Description of the Related Art

Absorbent articles such as infant diapers, training pants, adult incontinence products, and the like are well known. The prior art has considered various methods of inhibiting or preventing leakage.

For example, U.S. Pat. No. 4,938,755 to Foreman discloses a diaper having a containment pocket formed by a barrier cuff mounted e.g. from the outer edge of the diaper. The barrier cuff attempts to prevent exudates from flowing outwardly from the diaper.

U.S. Reissue Pat. No. 33,106 to Beckestrom discloses a pair of combined leg cuffs/containment flaps formed by the liquid impermeable outer cover of the diaper.

U.S. Pat. No. 4,681,579 to Toussant et al. discloses a diaper providing containment reservoirs wherein glue spots secure portions of the side flaps to the topsheet thereby minimizing the size of the openings to the containment reservoir. The outer sides of the crotch portion of the diaper includes an outwardly directed fold.

It is an objective of the invention to provide an absorbent article with reservoirs formed by folded containment flaps to prevent exudates from leaking around or over the containment flaps and out of the absorbent article.

SUMMARY OF THE INVENTION

In one aspect, the present invention resides in an absorbent article having a front portion, a rear portion, a crotch portion connecting the front and rear portions, and a longitudinal axis extending through the center of the front, rear and crotch portions, the crotch portion having opposing first and second longitudinal side portions, the absorbent article comprising an outer cover; a bodyside liner, the bodyside liner and the outer cover, in combination, being joined into, and thus being at least part of a base structure; an absorbent core located between the bodyside liner and the outer cover; and first and second containment flaps extending longitudinally of the absorbent article in the crotch portion, a first proximal edge of the first containment flap being attached to the base structure near the first longitudinal side portion, a second proximal edge of the second containment flap being attached to the base structure near the second longitudinal side portion, a first distal edge of the first containment flap having front and rear elements thereof attached to the base structure to form a first C-fold within the crotch portion, a second distal edge of the second containment flap having front and rear elements thereof attached to the base structure to form a second C-fold within the crotch portion, the respective distal edges being unattached to the base structure within the crotch portion of the absorbent article, the first and second containment flaps having respective first inner and second outer surfaces at the first and second C-folds, the inner surfaces facing inwardly toward the longitudinal axis to form first and second containment reservoirs within the containment flaps, the absorbent article having first and second opposing outer edges in the crotch portion, the containment reservoirs extending outwardly, at the C-folds, of the proximal edge, toward the outer edge.

In some embodiments, the absorbent article further comprises a pair of longitudinally extending leg cuffs including leg elastics located outwardly from the crotch portion and comprised in respective ones of the longitudinal side portions, wherein the containment flaps are attached to the base structure inwardly and spaced from the leg elastics.

In other embodiments, the containment flaps are attached to the base structure adjacent the leg elastics. The outward spacing of the containment flaps from the absorbent core allows for independent movement of the user's legs with substantially no effect upon the sealing effect of the absorbent article by the containment flaps. Part of the reason for independent movement is that the base structure outward of the absorbent core has more flexibility than the central crotch portion of the diaper.

The containment reservoirs are designed to contain at least 100 milliliters of exudates.

In another aspect of the invention, the base structure has a crotch side width between an outside edge of the absorbent core and an outer edge of the absorbent article, and each containment flap has an unfolded width greater than the crotch side width.

In some embodiments, each containment flap comprises a body-contact element at least in the crotch portion of the absorbent article to provide a greater gasketing effect due to surface contact between the body-contact element and the user's body rather than a line contact. Further, the body-contact element may include flap elastics formed by an elastic material to enhance the gasketing effect with the user's body. The body-contact element preferably has a width greater than two centimeters so the surface contact is sufficient to provide a gasketing effect. Preferably, the body-contact element is attached to the respective distal edge of the containment flaps. The body-contact element may comprise at least three strands of elastic material spaced apart to maintain surface contact with the user's body. The body contact element may also comprise a portion of the containment flap.

The body-contact element or containment flap may also include, in some embodiments, flap elastics which are mounted near the distal edge of each of the first and second containment flaps, such that the containment flaps form surface contact with the user's body. The containment flaps may be made from the same material as the outer cover.

Some embodiments of the invention further include an arrangement wherein the containment flaps have a greater level of tension than the leg cuffs including leg elastics. The tension is greater because of the number of elastics, the position at attachment to the containment flaps in at least the crotch portion of the absorbent article and the degree of elongation at attachment. This increased tension does not allow the containment flaps to lay flat when the absorbent article is installed on the user. Therefore, overflow protection is afforded by the containment reservoir formed by the increased tension.

In another embodiment, the absorbent article has a length along the longitudinal axis, and the open space defined by each containment flap, at the opening to the respective containment reservoir, has a longitudinal length less than two thirds the longitudinal length of the absorbent article when the absorbent article is stretched along the longitudinal length thereof. Preferably, the open space of each containment flap has a longitudinal length approximately one half the longitudinal length of the absorbent article when the absorbent article is stretched along the longitudinal length thereof.

The invention further comprehends an absorbent article having a front portion, a rear portion, a crotch portion connecting the front and rear portions, and a longitudinal axis extending through the front, rear and crotch portions, the crotch portion having a length, and opposing first and second longitudinal side portions, the absorbent article comprising an outer cover; a bodyside liner, the bodyside liner and the outer cover forming, in combination, a base structure; an absorbent core located between the bodyside liner and the outer cover; and first and second containment flaps extending longitudinally of the absorbent article in the crotch portion, a first proximal edge of the first containment flap being attached to the base structure and spaced outwardly from the absorbent core in the crotch portion at the first longitudinal side portion, a second proximal edge of the second containment flap being attached to the base structure at the second longitudinal side portion and spaced outwardly from the absorbent core in the crotch portion, the distal edge of the first containment flap having front and rear elements thereof attached to the base structure to form a first C-fold within the crotch portion of the absorbent article, the distal edge of the second containment flap having front and rear elements thereof attached to the base structure to form a second C-fold within the crotch portion of the absorbent article, the respective distal edges being unattached to the base structure within the crotch portion of the absorbent article, the first and second containment flaps having respective first inner and second outer surfaces at the first and second C-folds, the respective inner surfaces facing inwardly toward the longitudinal axis to form respective first and second containment reservoirs within the respective containment flaps, each containment flap respectively providing an open space opening into the respective containment reservoirs, between the respective distal edge and the base structure, the open space extending along substantially the entire length of the crotch portion when the absorbent article is applied to a user's body.

The invention further comprehends an absorbent article having a front portion, a rear portion, a crotch portion connecting the front and rear portions, and a longitudinal axis extending through the front, rear and crotch portions, the crotch portion having opposing first and second longitudinal side portions, the absorbent article comprising an outer cover; a bodyside liner, the bodyside liner and the outer cover forming, in combination, a base structure; an absorbent core located between the bodyside liner and the outer cover; first and second containment flaps extending longitudinally in the crotch portion, a first proximal edge of the first containment flap being attached to the base structure near the first longitudinal side portion, a second proximal edge of the second containment flap being attached to the base structure near the second longitudinal side portion, a first distal edge of the first containment flap having front and rear elements thereof attached to the base structure to form a first C-fold within the crotch portion, a second distal edge of the second containment flap having front and rear elements thereof attached to the base structure to form a second C-fold within the crotch portion, the respective distal edges being unattached to the base structure within the crotch portion of the absorbent article; and flap elastics mounted to the containment flaps near the distal edge of each containment flap and extending longitudinally with the containment flaps along at least the crotch portion of the absorbent article, the first and second containment flaps having respective first inner and second outer surfaces at the first and second C-folds, the inner surfaces facing inwardly toward the longitudinal axis to form respective first and second containment reservoirs within the containment flaps and the flap elastics being positioned near the distal edge of the containment flaps to urge the distal edges of the containment flaps against a user's body thereby to provide a gasketing effect. Preferably, the flap elastics are not attached to the base structure.

The invention further comprehends an absorbent article having a front portion, a rear portion, a crotch portion connecting the front and rear portions, and a longitudinal axis extending through the front, rear and crotch portions, the crotch portion having opposing first and second longitudinal side portions, the absorbent article comprising an outer cover; a bodyside liner, the bodyside liner and the outer cover forming, in combination, a base structure; an absorbent core located between the bodyside liner and the outer cover; first and second containment flaps extending longitudinally in the crotch portion of the absorbent article, a first proximal edge of the first containment flap being attached to the base structure at the first longitudinal side portion, a second proximal edge of the second containment flap being attached to the base structure at the second longitudinal side portion, a first distal edge of the first containment flap having front and rear elements thereof attached to the base structure to form a first C-fold within the crotch portion of the absorbent article, a second distal edge of the second containment flap having front and rear elements thereof attached to the base structure to form a second C-fold within the crotch portion of the absorbent article, the base structure having first and second crotch side widths between outer edges of the absorbent core and respective first and second outer edges in the crotch portion of the absorbent article, each containment flap having an unfolded width greater than the respective crotch side width, the first and second containment flaps having respective first inner and second outer surfaces at the respective first and second C-folds, the inner surfaces facing inwardly toward the longitudinal axis to form first and second containment reservoirs within the respective containment flaps, each containment flap respectively providing an open space extending along substantially the entire length of the crotch portion when the absorbent article is applied to a user's body, each containment reservoir extending substantially across the crotch side width from both of the proximal and distal edges to the C-fold. Preferably, the width of the containment flap is approximately 1.5 times the crotch side width.

BRIEF DESCRIPTION OF THE DRAWINGS

FIG. 3 illustrates a cross-sectional view taken at line 3—3 in FIG. 2 where the containment flaps are attached to the absorbent article at both the distal edge and the proximal edge.

FIG. 4 illustrates a cross-sectional view taken at line 4—4 in FIG. 2 where the containment flaps are attached to the base structure only at the proximal edge.

Figure 1:
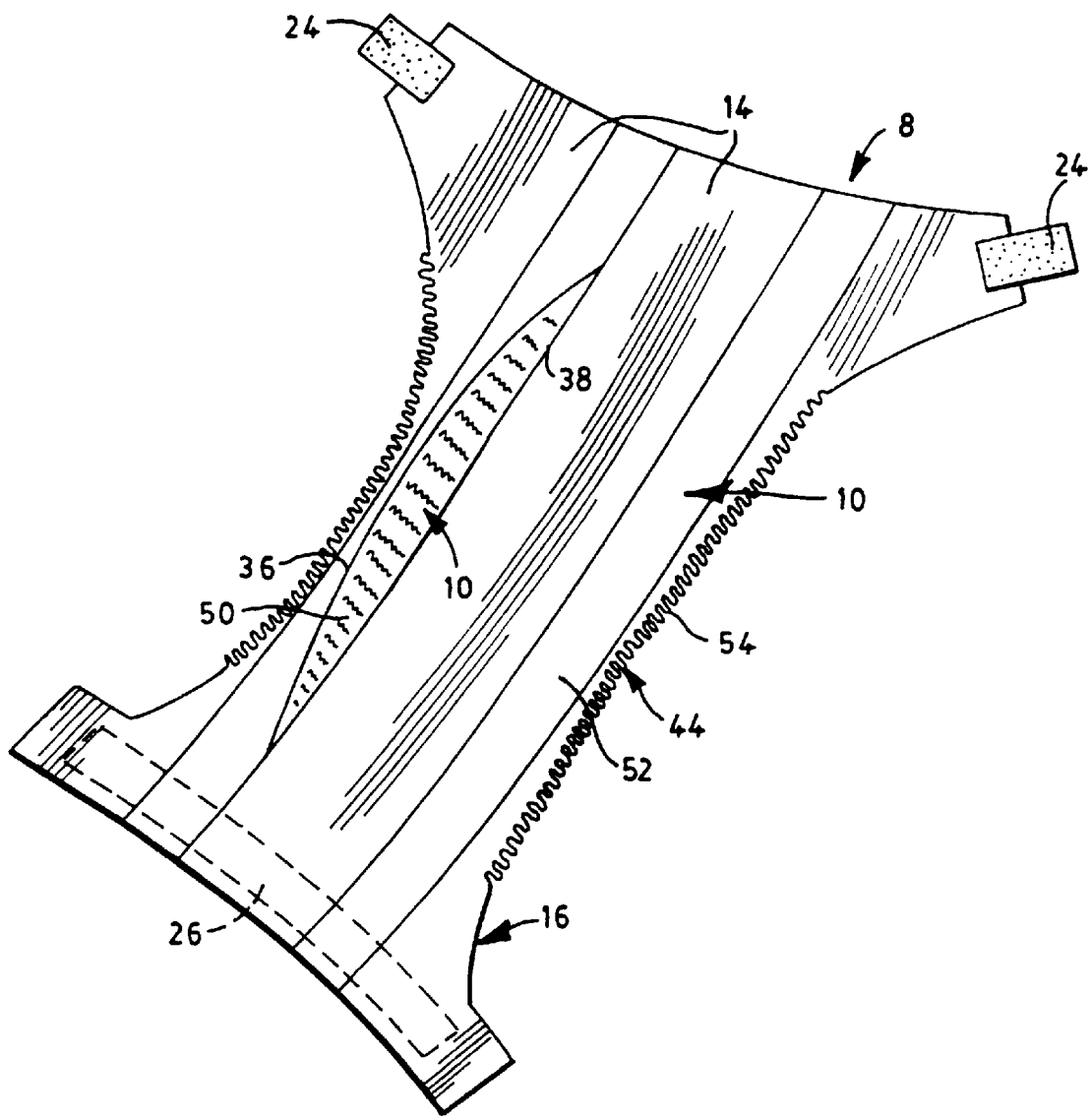
FIG. 1 illustrates an absorbent article according to the present invention.

The invention is not limited in its application to the details of construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE PREFERRED EMBODIMENTS

Applicants' invention comprises an absorbent article 8 with void volume containment flaps 10 as shown in FIG. 1. The absorbent article 8 includes an outer cover 12 with a bodyside liner 14 attached thereon to form, in combination, at least part of base structure 16 as shown in FIG. 4. FIG. 4 also illustrates containment flaps 10 including flap elastics 18 forming a void volume containment reservoir 20 to contain an overflow of exudates and prevent leakage. An absorbent core 22 is mounted between the bodyside liner 14 and outer cover 12 in the center of the absorbent article 8. FIG. 1 illustrates an attachment mechanism, such as hook and loop fasteners 24, 26 for securing the absorbent article 8 to the lower torso of a user. The first fastener 24 comprises a mechanical fastener such as the hooks of a hook and loop fastening system mounted on the base structure 16. The second fastener 26 comprises a corresponding loop material attached to the outer cover 12 and adapted to releasably engage with the hook material of the first fastener 24. Other well known fasteners and the like may be used to support the absorbent article upon a user.

A suitable bodyside liner 14 may be manufactured from a wide selection of web materials, such as porous foams, reticulated foams, apertured plastic films or natural fibers. For example, the bodyside liner 14 may comprise wood or cotton fibers. Other possible materials are synthetic fibers, such as polyester or polypropylene fibers, or a combination of natural and synthetic fibers. Bodyside liner 14 is suitably utilized to help isolate the liquids held in the absorbent core 22 from the wearer's skin.

Various woven and nonwoven fabrics may be used for bodyside liner 14. For example, bodyside liner 14 may be composed of a meltblown or spunbonded web of polyolefin fibers. The bodyside liner 14 may also comprise a carded and/or bonded web composed of natural and/or synthetic fibers. The bodyside liner 14 may also be composed of a substantially hydrophobic material wherein the hydrophobic material is treated with a surfactant or otherwise processed to impart a desired level of wettability and hydrophilicity. In a particular embodiment of the present invention, the bodyside liner 14 may comprise a nonwoven, spunbonded, polypropylene fabric composed of about 2.8–3.2 denier fibers formed into a web having a basis weight of about 22 grams per square meter and a density of about 0.06 grams per cubic centimeter. The fabric is then surface treated with about 0.3 weight percent of a surfactant. The bodyside liner 14 may comprise a multiplicity of components or layers which correspond to any of the materials disclosed herein, as well as others known in the art.

It is generally preferred that the outer cover 12 of the absorbent article 8 be formed from a material which is substantially impermeable to liquids. A typical outer cover 12 may be manufactured from a thin plastic film or other flexible liquid-impermeable material. For example, the outer cover 12 may be formed from a polyethylene film having a thickness of from about 0.012 millimeters to about 0.051 millimeters. If the outer cover 12 should have a more clothlike feeling, it may comprise a polyethylene film laminated to a surface of a nonwoven web, such as a spunbonded web of polyolefin fibers. For example, a polyethylene film having a thickness of about 0.015 millimeters may have thermally or otherwise laminated thereto a spunbond web of polyolefin fibers having a thickness from 1.5 to 2.5 denier per filament, which nonwoven web has a basis weight of about 24 grams per square meter. Further, the outer cover 12 may be formed of a woven or nonwoven fibrous web which has been totally or partially constructed or treated to impart a desired level of liquid impermeability to selected regions that are adjacent or proximate the absorbent core 22. Still further, the outer cover 12 may optionally be composed of a micro-porous material which permits vapors to escape from the absorbent core 22 and through outer cover 12 while preventing liquid exudates from passing through the outer cover 12.

The absorbent core 22 suitably comprises a matrix of hydrophilic fibers, such as a web of cellulosic fluff, in combination with a high-absorbency material commonly known as superabsorbent material. In a particular embodiment, absorbent core 22 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core 22.

Alternatively, the absorbent core 22 may comprise a laminate of fibrous webs and superabsorbent material or other suitable means of maintaining a superabsorbent material in a localized area.

The absorbent core 22 may have any of a number of shapes. For example, the absorbent core 22 may be rectangular, I-shaped or T-shaped. It is generally preferred that the absorbent core 22 be narrower in the crotch portion 28 than the rear portion 30 or front portion 32.

The high-absorbency material in the absorbent core 22 can be selected from natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Figure 2:
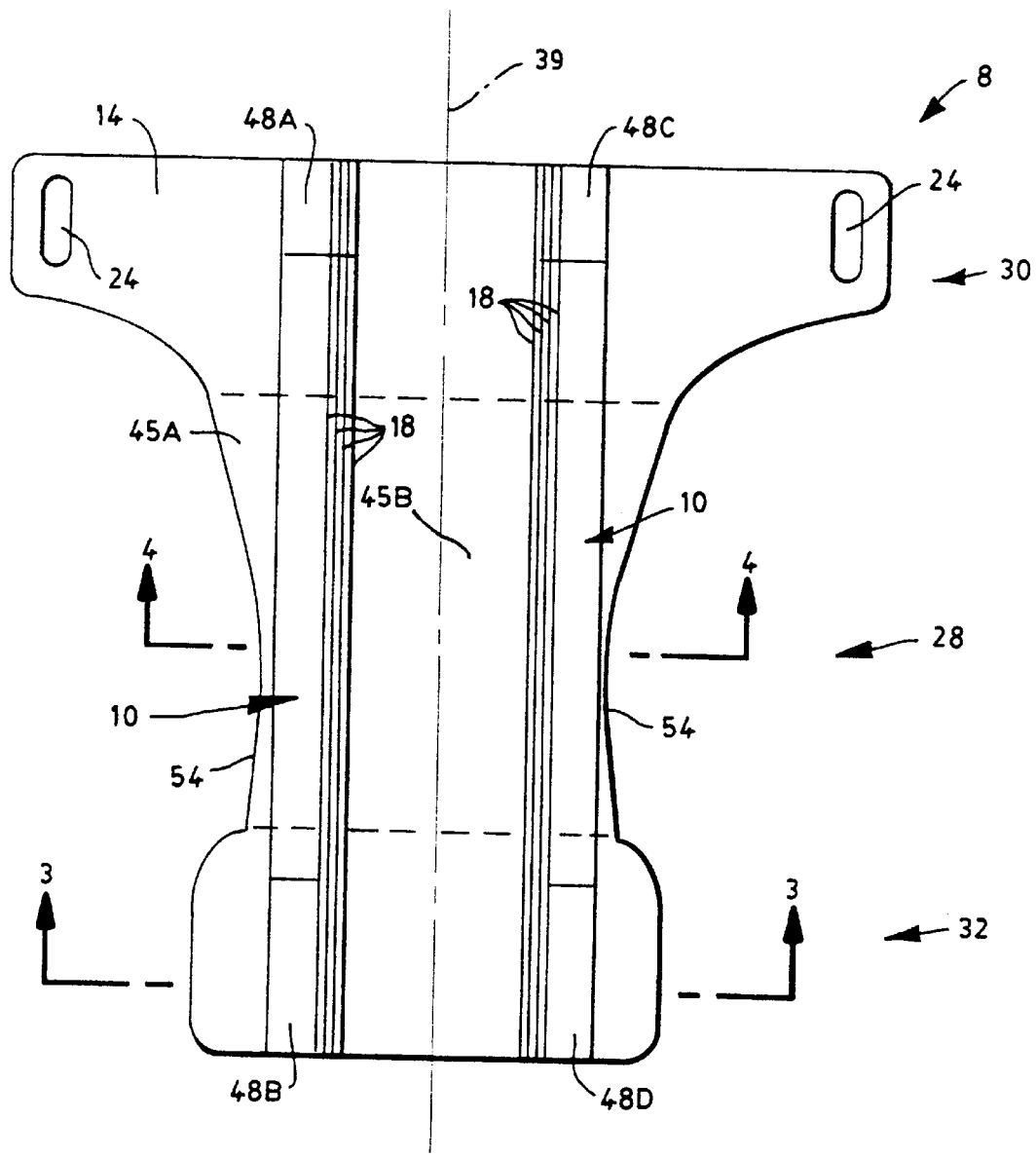
FIG. 2 illustrates a top plan view of an absorbent article according to the present invention.
Figure 9:
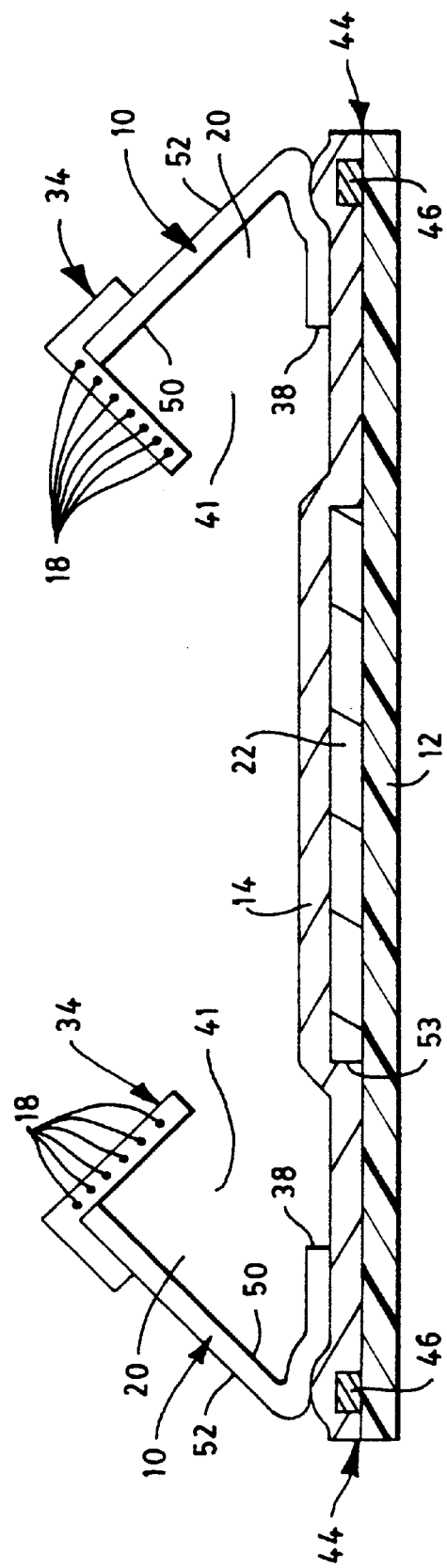
FIG. 9 illustrates another embodiment of the containment flaps wherein the body-contact element comprises a separate component, mounted upon the containment flap.

The containment flaps 10 may include flap elastics 18 as shown in FIGS. 2, 4 and 9. The containment flaps 10 are joined to the bodyside liner 14 by heat sealing, sonic bonding, adhesive bonding or the like. Adhesive bonding includes the use of glue lines or other glue patterns and/or arrangements.

The flap elastics 18 shown in the drawings shape the containment flaps 10 in use, to form containment reservoir 20. The flap elastics 18 may comprise one or more individual strands of elastomeric material. For example, FIG. 9, shows six parallel, spatially separated strands of elastomeric material which, along with a separate piece of sheet or laminate material, form body-contact element 34 separate from the containment flap. The separate body-contact element 34 is glued or otherwise attached to the containment flap 10. The body-contact element 34 forms a surface contact with the user's body, to prevent leakage of exudates, rather than a line contact. Similarly, FIG. 4 illustrates another embodiment wherein the flap elastics 18 comprise three parallel, spatially separated strands which form a body-contact element 34 integral with, or part of the containment flap 10. The purpose of multiple strands, once again, is to create a surface contact with the user's body which decreases the possibility of leakage of exudates from the absorbent article 8. Preferably the width of the area containing elastic strands is at least two centimeters to create the desired surface contact. Further, it is preferred that at least three strands of elastomeric material are utilized to form the body-contact element.

Another way of providing the elastic property in the containment flap is to use a sheet of material having an appropriate elasticity and width to create a surface contact with the user's body. Such a material, for example, may comprise a stretch-bonded laminate. A stretch-bonded laminate comprises at least a two layered composite in which one layer is a gatherable layer and the other layer a stretchable layer. The layers are joined together when the stretchable layer is in a stretched condition so that, upon relaxing the layers, the gatherable layer is gathered. The stretchable layer can be a film of stretchable material, such as a layer of styrene ethylene butylene styrene or other elastomeric polymer, or a plurality of strands of a stretchable material such as latex. Other materials with similar properties may also be provided integral with or attached to the containment flap 10.

The flap elastics 18 may be distributed over the full width of the containment flap and formed of a resiliently deformable elastomer, or elastomer-like material. Preferably, the flap elastics 18 are placed at the distal edge 36 of the containment flap to help form a C-fold flap when attached to front portion 32 and rear portion 30 of the base structure 16 at bodyside liner 14. The proximal edge 38 of the containment flap 10 is attached to the bodyside liner 14 of base structure 16 upon a longitudinal side portion thereof, along a line extending in a longitudinal direction generally parallel to the longitudinal axis 39. The flap elastics 18 may run the entire length of the containment flap 10. In the embodiment of FIGS. 2–4, the containment flaps 10 and flap elastics 18 are present only in the crotch portion 28 of the absorbent article 8. As illustrated in FIG. 3, the flap elastics 18 are not present in the front portion 32 or rear portion 30 of the absorbent article 8. Preferably, the flap elastics 18 are mounted in the crotch portion 28 along the distal edge 36 of each respective containment flap 10 to provide a "bucket effect" which causes distal edges 36 to become spaced from the bodyside liner 14 when the absorbent article 8 is mounted upon the user's body, whereby the C-folded containment flaps 10 define an open space 41 between the proximal edges 38 and the distal edges 36, thereby forming reservoir 20 when the absorbent article is placed upon a user's body. This bucket effect is caused in part by the flap elastics 18 being mounted upon the containment flap 10 in a stretched condition. As a result, the containment flap 10 tends to position itself in a spaced relation away from the bodyside liner 14 toward a generally upright and approximately perpendicular configuration as shown by the cross-sectional view in FIGS. 4, 5 and 9. Further, the view of the left containment flap 10 as shown in FIG. 1 also illustrates the "bucket effect" created by the stretched flap elastics 18.

Suitable flap elastics 18 for applicants' invention may, for example, be composed of a 470 decitex LYCRA® elastomer, 620 decitex LYCRAs elastomer or other elastomers with suitable characteristics.

Figure 6:
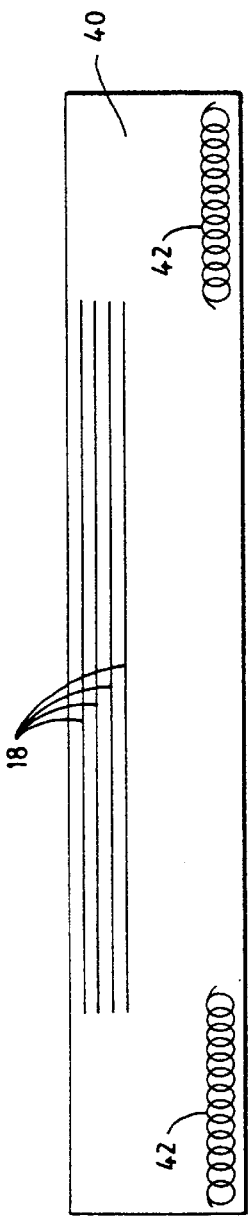
FIG. 6 illustrates a plan view of a design for a containment flap useful with the absorbent article disclosed herein.
Figure 7:
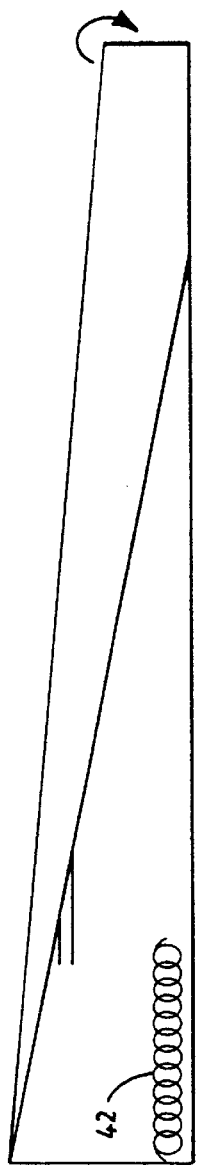
FIG. 7 illustrates a plan view of the containment flap shown in FIG. 6 in the process of being folded to create a C-fold.
Figure 8:
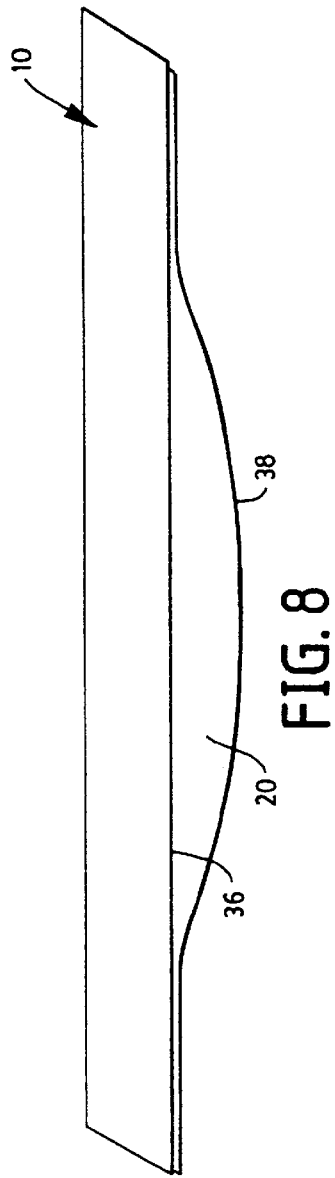
FIG. 8 illustrates a pictorial view of the containment flap shown in FIGS. 6 and 7 partially retracted.

The containment flaps 10 may be constructed of a material which is the same as, or different than the material comprising outer cover 12. The containment flaps 10 are preferably liquid impervious. The containment flaps 10 may be formed from a polymeric film material or from e.g. a nonwoven material which has been treated so as to be liquid impervious. The containment flaps 10 may be formed by a single or multiple layer flap material 40 with appropriate flap elastics 18 secured thereto as shown in FIGS. 6–8. In the plan view of FIG. 6, the stretched or extended flap elastics 18 are glued or otherwise attached to the containment flap 10. Glue 42 is then added to a lower end of the flap material 40. The flap material 40, while in an extended or stretched-to-stop condition, is then folded over in half to form the containment flap 10 as sequentially illustrated in FIGS. 7 and 8. The pictorial view of FIG. 8 then shows the containment flap 10 in a partially relaxed condition. The proximal edge 38 and the distal edge 36 of the containment flap 10 are viewable in the illustrated partially relaxed condition, thus partially opening the reservoir 20.

Other arrangements of the containment flaps 10 are contemplated. For example, the flap material may fold over only a small portion of itself when forming the containment flap. Further, as shown in FIG. 9, a separate piece of material may comprise the body-contact element 34 which forms a surface contact with the user's body. The body-contact element 34, if it comprises a separate element, may be formed by materials the same as or similar to those comprising the containment flap 10. Further, where the body contact element 34 is a separate piece of material, and contains the elastics 18, the base element 43 of containment flap 10 (See FIG. 9) may be devoid of any elastics.

Leg cuffs 44 are suitably formed by portions of the outer cover 12 and the bodyside liner 14, which extend transversely outward of the longitudinal side portions of the absorbent core 22. The leg cuffs 44 may also be formed from separate materials which are attached to the outer cover 12 and/or the bodyside liner 14. Leg cuffs 44 include leg elastics 46. Materials suitable for forming leg elastics 46 include strands, ribbons or one or more layers of a polymeric and/or elastomeric material which may be adhered in the absorbent article 8 at the leg cuff 44 while in a stretched position. Alternatively, the material can be attached, in a relaxed condition, to the absorbent article 8 while the absorbent article 8 is pleated, as shown in FIG. 1, such that elastic constrictive forces are imparted to the leg cuff 44 when the leg cuff 44 is elongated along axis 39. The leg elastics 46 shown in FIGS. 4, 5 and 9 may be made of material similar or identical to the flap elastics 18.

FIGS. 2–4 illustrate the inwardly facing C-fold containment flaps of applicants' invention. The proximal edge 38 of the containment flap 10 is glued, bonded or otherwise attached to the base structure 16 in a pattern, e.g. a line, extending in a longitudinal direction generally parallel to the longitudinal axis 39. As shown in FIG. 2, longitudinal axis 39 defines first and second longitudinal side portions 45A, 45B in the crotch portion 28.

As shown in the cross-sectional view of FIG. 3, taken along the line 3—3 in FIG. 2, glue 42 attaches a top portion 47 of the respective containment flap 10 to a bottom portion 49 thereof on both ends of the respective containment flap 10. These regions of attachment 48A, 48B, 48C, 48D are more clearly shown in the top view of FIG. 2. The regions of attachment 48A, 48B, 48C, 48D show where the top portion 47 of the containment flap 10 has front and rear elements thereof attached to either the base structure 16 or to another portion of the containment flap 10 itself. The flap elastics 18 shown in FIG. 2 are typically stretched when attached to then form the "bucket effect" more clearly shown in FIG. 1. In FIG. 1, a first inner surface 50 of the containment flap 10 is shown forming the open space for exudates. The inner surfaces 50 of the containment flaps 10 face inwardly to form the respective inner surfaces of containment reservoirs 20. Further, an outer surface 52 of the containment flap is also illustrated.

Flap elastics 18 are preferably mounted to the distal edge 36 of the containment flap 10 only in the crotch portion 28 of the absorbent article 8 as described earlier. The containment reservoir 20 shown in FIG. 3 is then formed by the flap elastics 18 raising or lifting the respective containment flap 10 when the absorbent article 8 is mounted on the user's body.

Figure 10:
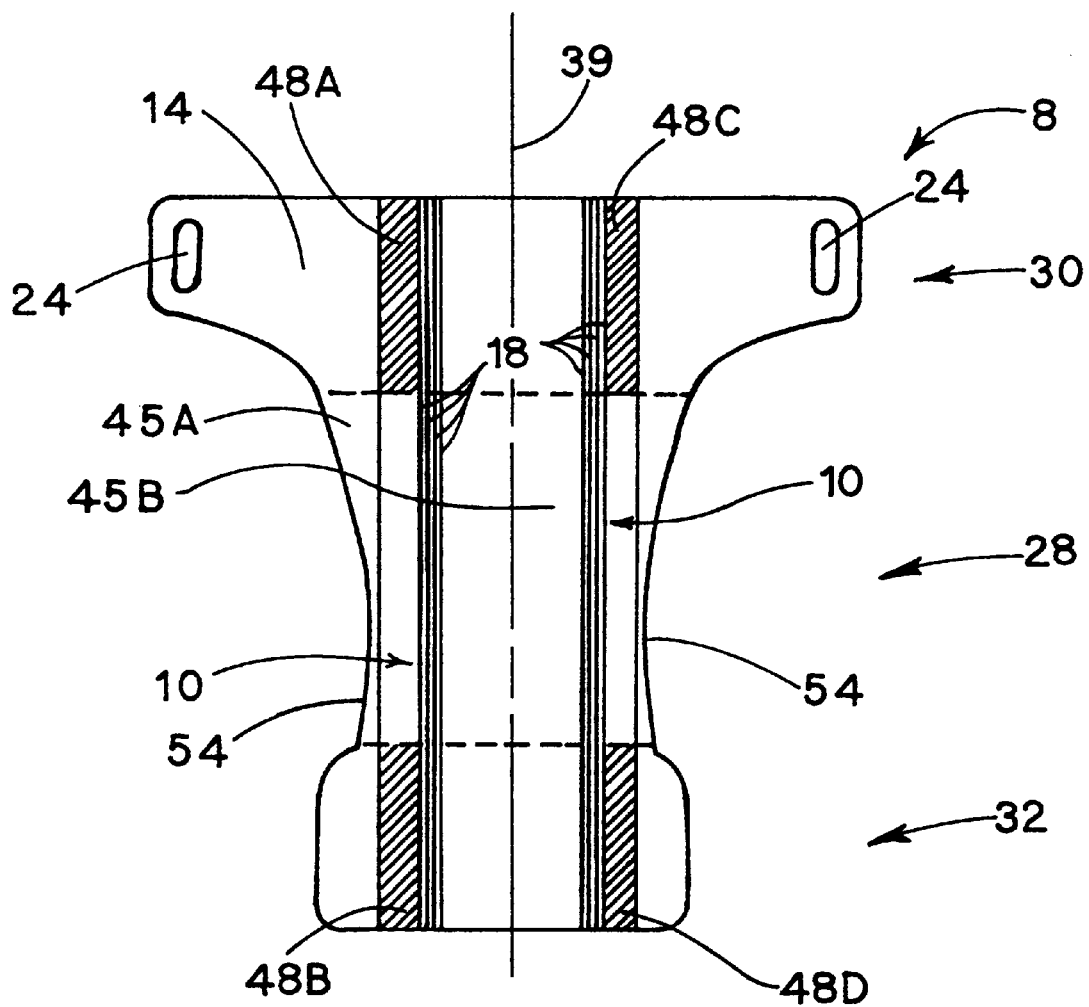
FIG. 10 illustrates a top plan view of another absorbent article according to the present invention.

The longitudinal length of the open space 41 (See FIG. 5) forming the containment reservoir 20 covers substantially the entire length of the crotch portion 28. FIG. 2 shows the entire lengths of the containment flaps 10 and the regions of attachment 48A, 48B, 48C, 48D where the distal edges 36 are glued to the proximal edges 38 at longitudinal extremities of the containment flaps 10. Preferably, the open space 41 along the length of each containment flap 10, such as between regions 48A and 48B, provides an open entrance into the respective reservoir 20, between the distal edge 36 and the base structure 16. Preferred length for open space 41 is less than two thirds the longitudinal length of the absorbent article 8 when the article is stretched along the longitudinal axis 39 thereof. A highly preferred length for open space 41 of the reservoir 20, formed by the containment flap 10, is approximately one half of the longitudinal length of the absorbent article 8. FIG. 10 illustrates such an arrangement. The regions of attachment 48A, 48B, 48C, 48D disposed upon the front portion 32 and rear portion 28 of the absorbent article 8 may be varied. However, applicants generally prefer that the front portion 32 of the absorbent article 8 has larger regions of attachment 48B, 48D than the regions 48A, 48C on rear portion 28.

Figure 5:
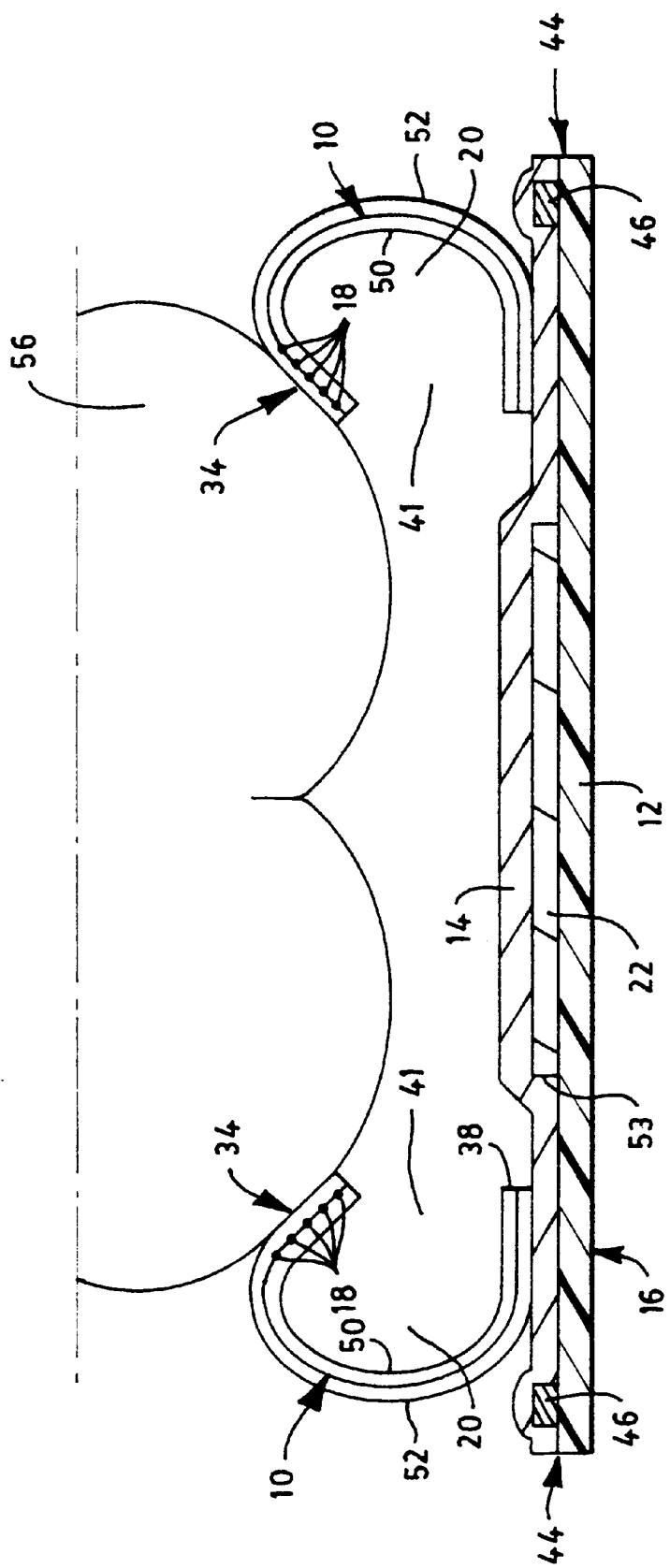
FIG. 5 illustrates another cross-sectional view showing surface contact between the body-contact element and a user's body.

The position of the containment flaps 10 with respect to the absorbent core 22 or the longitudinal axis 39 is an important aspect of the invention. While the containment flaps 10 can be placed upon the absorbent core 22, that arrangement does not provide as great a benefit as other locations. As shown in FIGS. 3 and 4, the containment flaps 10, and especially proximal edges 38, are spaced outwardly preferably no greater than one inch from the edge of the absorbent core 22. This mounting location, in combination with opening the containment flaps 10 inwardly, greatly enhances the ability of the reservoir 20 to entrap exudates, as well as enhancing the amount of exudates which can be contained in the respective reservoirs 20. Due to this arrangement, at least approximately 100 milliliters of fecal material or other solid or semi-solid material can be received and contained in the respective containment reservoirs 20. FIG. 5 shows spacing the containment flaps 10 outwardly from the absorbent core 22 an even greater distance than in the FIG. 4 embodiment. FIG. 9 shows mounting the containment flaps 10 upon the leg cuff 44 and flap elastics 46. This arrangement helps maximize the capacity of containment reservoirs 20 formed by the containment flap 10. Opening the containment flaps 10 inwardly, as shown in FIGS. 4, 5 and 9 is also crucial in maximizing the capacity of containment reservoir 20. Thus FIGS. 4, 5 and 9 represent separate embodiments wherein the containment flaps 10 are mounted further outwardly in FIG. 5 than in FIG. 4, and further outwardly in FIG. 9 than in FIG.5

Mounting the containment flaps 10 on the base structure 16 outwardly from the absorbent core allows for more independent movement of the user's legs with substantially no effect upon the sealing effect. This occurs at least in part because the base structure 16 is more flexible and movable when located outwardly from the absorbent core 22.

The width of the containment flap 10 in the crotch portion 28 of the absorbent article 8 is important to the sealing effect provided by the containment flap 10. The unfolded width of the containment flap 10 preferably is greater than the crotch side width taken from an edge 53 of the absorbent core 22 to a respective outer edge 54 of the absorbent article 8 along line 4—4 of FIG. 2 in the crotch portion 28. This increased width, as compared to conventional diapers, increases the sealing effect of the containment flaps 10. Preferably, the unfolded width of the containment flap 10 is about 1.5 times the crotch side width of the absorbent article 8.

The containment flaps 10 preferably also have a first level of tension greater than the level of tension of the leg cuffs 44 defined by leg elastics 46 when the absorbent article is mounted upon a user's body, because of the number of strands of flap elastics 18 and their stretched attachment to e.g. the distal edge 36 of the containment flaps 10. This tension does not allow the containment flaps 10 to lie flat against the bodyside liner 14. Instead, the containment flaps 10 generally form a bucket shape when applied to the user's body.

Forming a surface contact between the distal edges 36 and the user's body also impedes the leakage of exudates from the absorbent article 8. As shown in FIG. 5, the containment flaps 10 form surface contact with the user's body 56 via the body-contact element 34. In the containment flaps illustrated in FIG. 5, at least two of flap elastics 18 are effectively substantially equally spaced from the body of the user. This is due to the C-fold arrangement of the containment flaps 10 and the multiple strands forming flap elastics 18. The flap elastics 18 provide surface contact with the user's body 56. The arrangement of FIG. 5 generally prevents leakage of exudates regardless of the presence or absence of leg elastics 46. Accordingly, in some embodiments, leg elastics 46 may be omitted.

FIG. 10 shows an embodiment similar to the embodiment of FIG. 2 (like elements have like reference numerals) Regions of attachment 48A, 48B, 48C, 48D show where containment flaps 10 have glue attaching top portions of the respective containment flaps to respective underlying bottom portions thereof. The open spaces between top and bottom portions of the respective containment flaps in FIG. 10 extend along the crotch portion of absorbent article 8, and not along any part of front portion 32 or rear portion 30. Thus the open space of each containment flap 10 has a longitudinal length approximately one half the longitudinal length of the entire absorbent article when the absorbent article is fully stretched along longitudinal axis 39, as shown in FIG. 10.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

Having thus described the invention, what is claimed is:

1. An absorbent article having a front portion, a rear portion, a crotch portion connecting said front and rear portions, and a longitudinal axis extending through said front, rear and crotch portions, said crotch portion having opposing first and second longitudinal side portions, said absorbent article comprising:

(a) an outer cover;
    (b) a bodyside liner, said bodyside liner and said outer cover, in combination, being joined into, and thus being at least part of, a base structure;
    (c) an absorbent core located between said bodyside liner and said outer cover;
    (d) first and second containment flaps extending longitudinally of said absorbent article in said crotch portion, a first proximal edge of said first containment flap being attached to said base structure at said first longitudinal side portion, a second proximal edge of said second containment flap being attached to said base structure at said second longitudinal side portion,
    (e) a pair of longitudinally extending leg cuffs including leg elastics located outwardly in said crotch portion and comprised in respective said longitudinal side portions, said containment flaps having a first level of tension in said crotch portion, and said leg cuffs having a second level of tension in said crotch portion, when said absorbent article is mounted upon a body of a user, the first level of tension being greater than the second level of tension.

2. An absorbent article of claim 1 wherein said proximal edges of said containment flaps are attached to said base structure inwardly and spaced from said leg elastics.

3. An absorbent article of claim 1, a first distal edge of said first containment flap having front and rear elements thereof effectively attached to said base structure to form a first C-fold with said crotch portion, a second distal edge of said second containment flap having front and rear elements thereof effectively attached to said base structure to form a second C-fold within said crotch portion, said respective distal edges being effectively unattached to said base structure within said crotch portion.

4. An absorbent article of claim 1 wherein said proximal edges of said containment flaps are attached to said base structure adjacent said leg elastics.

5. An absorbent article of claim 1 wherein outward spacing of said first and second proximal edges of said first and second containment flaps from said absorbent core allows for movement of the user's legs independent of any sealing effect between said absorbent article and the body of a user at said containment flaps.

6. An absorbent article of claim 3, said first and second containment flaps having respective first inner and second outer surfaces at the respective said first and second C-folds, the respective said inner surfaces facing inwardly toward the longitudinal axis and thus toward first and second containment reservoirs within the respective said containment flaps, said absorbent article having first and second opposing outer edges in said crotch portion, said containment reservoirs extending outwardly of the respective said proximal edges of the respective said containment flaps, toward the respective said outer edges, and each said containment flap respectively providing an open space extending along said crotch portion when said absorbent article is applied to a user's body.

7. An absorbent article of claim 6 wherein flap elastics are mounted near said distal edge of each of said first and second containment flaps, such that said containment flaps provide surface contact with the user's body.

8. An absorbent article of claim 1 wherein said containment flaps are made from the same material as said outer cover.

9. An absorbent article of claim 1, said base structure having a crotch side width between said absorbent core and an outer edge of said absorbent article, and wherein each said containment flap has an unfolded width greater than said crotch side width.

10. An absorbent article of claim 1, each said containment flap comprising a body-contact element at least in said crotch portion of said absorbent article to provide a greater gasketing effect due to surface contact between said body-contact element and the user's body.

11. An absorbent article of claim 10 wherein said body-contact element further comprises an elastic material to enhance gasketing with the user's body.

12. An absorbent article of claim 6, said absorbent article having a length along the longitudinal axis, and wherein the open space of each said containment flap has a longitudinal length less than two thirds the longitudinal length of said absorbent article when said absorbent article is stretched along the longitudinal axis.

13. An absorbent article of claim 12 wherein the open space of each said containment flap has a longitudinal length approximately one half the longitudinal length of said absorbent article when said absorbent article is stretched along the longitudinal axis.

14. An absorbent article having a front portion, a rear portion, a crotch portion connecting said front and rear portions, and a longitudinal axis extending through said front, rear and crotch portions, said crotch portion having a length, and opposing first and second longitudinal side portions, said absorbent article comprising:

(a) an outer cover;
    (b) a bodyside liner, said bodyside liner and said outer cover, in combination, being joined into, and thus being at least part of, a base structure;
    (c) an absorbent core located between said bodyside liner and said outer cover;
    (d) first and second containment flap s extending longitudinally of said absorbent article in said crotch portion, a first proximal edge of said first containment flap being attached to said base structure and spaced outwardly from said absorbent core in said crotch portion at said first longitudinal side portion, a second proximal edge of said second containment flap being attached to said base structure and spaced outwardly from said absorbent core in said crotch portion at said second longitudinal side portion, a first distal edge of said first containment flap having front and rear elements thereof effectively attached to said base structure to form said first containment flap in to the shape of a first C-fold within said crotch portion a second distal edge of said second containment flap having front and rear elements thereof effectively attached to said base structure to form said second containment flap into the shape of a second C-fold within said crotch portion, the respective said distal edges being effectively unattached to said base structure within said crotch portion, and (e) a pair of longitudinally extending leg cuffs including leg elastics located outwardly of said crotch portion and comprised in respective said longitudinal side portions, said containment flaps are attached to said base structure adjacent said leg elastics, said first and second containment flaps having respective first inner and second outer surfaces at the respective said first and second C-folds, the respective said inner surfaces facing inwardly toward the longitudinal axis and thus toward respective first and second containment reservoirs within the respective said containment flaps, each said containment flap respectively providing an open space opening into the respective said containment reservoir between the respective said distal edge and said base structure, said absorbent article having first and second opposing outer edges in said crotch portion, said containment reservoirs extending outwardly of the respective said proximal edges of the respective said containment flaps, toward the respective said outer edges.

15. An absorbent article of claim 14 wherein said absorbent article further comprises:

(e) a pair of longitudinally extending leg cuffs including leg elastics located outwardly of said portion and comprised in respective said longitudinal side portions, wherein said containment flaps are attached to said base structure inwardly from said leg elastics.

16. An absorbent article of claim 14, said containment flaps having a first level of tension in said crotch portion, and said leg cuffs having a second level of tension in said crotch portion, when said absorbent article is mounted to a body of a user, the first level of tension being greater than the second level of tension.

17. An absorbent article of claim 14 wherein said absorbent article further comprises:

(e) a pair of longitudinally extending leg cuffs including leg elastics located outwardly from the crotch portion and comprised in respective ones of said longitudinal side portions, wherein said containment flaps are attached to said base structure adjacent said leg elastics.

18. An absorbent article of claim 14 wherein said outward spacing of said containment flaps from said absorbent core allows for movement of the user's legs independent of any sealing effect between said absorbent article and the body of a user at said containment flaps.

19. An absorbent article of claim 14 wherein each of said containment reservoirs can contain at least 100 milliliters of exudates.

20. An absorbent article of claim 14 wherein flap elastics are mounted near said distal edge of each of said first and second containment flaps, such that said containment flaps provide surface contact with the user's body.

21. An absorbent article of claim 14, said base structure having a crotch side width between said absorbent core and the outer edge of said absorbent article, and wherein each said containment flap has an unfolded width greater than said crotch side width.

22. An absorbent article of claim 14, each said containment flap comprising a body-contact element at least in said crotch portion of said absorbent article to provide a greater gasketing effect due to surface contact between said body-contact element and the user's body.

23. An absorbent article of claim 22 wherein said body-contact element further comprises an elastomeric material to enhance gasketing with the user's body.

24. An absorbent article of claim 14, said absorbent article having a length along the longitudinal axis, and wherein the open space of each said containment flap has a longitudinal length less than two thirds the longitudinal length of said absorbent article when said absorbent article is stretched along the longitudinal axis.

25. An absorbent article of claim 24 wherein the open space of each said containment flap has a longitudinal length approximately one half the longitudinal length of said absorbent article when said absorbent article is stretched along the longitudinal axis.

26. An absorbent article having a front portion, a rear portion, a crotch portion connecting said front and rear portions, and a longitudinal axis extending through said front, rear and crotch portions, said crotch portion having opposing first and second longitudinal side portions, said absorbent article comprising:

(a) an outer cover;

(b) a bodyside liner, said bodyside liner and said outer cover, in combination, being joined into, and thus being at least part of, a base structure;

(c) an absorbent core located between said bodyside liner and said outer cover;

(d) first and second containment flaps extending longitudinally of said absorbent article in said crotch portion, a first proximal edge of said first containment flap being attached to said base structure at said first longitudinal side portion, a second proximal edge of said second containment flap being attached to said base structure at said second longitudinal side portion, a first distal edge of said first containment flap having front and rear elements thereof effectively attached to said base structure to form a first C-fold within said crotch portion, a second distal edge of said second containment flap having front and rear elements thereof effectively attached to said base structure to form a second C-fold within said crotch portion, said respective distal edges being effectively unattached to said base structure within said crotch portion; and (e) a body-contact element attached to said distal edge of each said containment flap, each said body-contact element having a width great enough to conform to the body of the user at a contact surface.

27. An absorbent article of claim 26 wherein said body-contact element comprises at least three strands of elastic material, said strands being spaced apart to maintain said body contact element in surface contact with the user's body between said three strands of elastic.

28. An absorbent article of claim 26 wherein said absorbent article further comprises:

(e) a pair of longitudinally extending leg cuffs including leg elastics located outwardly from said crotch portion and comprised in respective said longitudinal side portions, wherein said containment flaps are attached to said base structure inwardly from said leg elastics.

29. An absorbent article of claim 28, said containment flaps having a first level of tension in said crotch portion, and said leg cuffs having a second level of tension in said crotch portion, when said absorbent article is mounted to a body of a user, the first level of tension being greater than the second level of tension.

30. An absorbent article of claim 26 wherein each said containment flap comprises the same material as said outer cover.

31. An absorbent article of claim 26, each said body-contact element comprising an elastomeric sheet of material to enhance gasketing to the user's legs.

32. An absorbent article of claim 31, wherein said elastomeric sheet of material comprises a stretch-bonded laminate.

33. An absorbent article of claim 26, wherein said body-contact element has a width greater than two centimeters so that surface contact is sufficient to provide a gasketing effect.

34. An absorbent article having a front portion, a rear portion, a crotch portion connecting said front and rear portions, and a longitudinal axis extending through said front, rear and crotch portions, said crotch portion having opposing first and second longitudinal side portions, said absorbent article comprising:

(a) an outer cover;

(b) a bodyside liner, said bodyside liner and said outer cover, in combination, being joined into, and thus being at least part of, a base structure;

(c) an absorbent core located between said bodyside liner and said outer cover; and (d) first and second containment flaps extending longitudinally of said absorbent article in said crotch portion, a first proximal edge of said first containment flap being attached to said base structure at said first longitudinal side portion, a second proximal edge of said second containment flap being attached to said base structure at said second longitudinal side portion, a first distal edge of said first containment flap having front and rear elements thereof effectively attached to said base structure to form a first C-fold within said crotch portion, a second distal edge of said second containment flap having front and rear elements thereof effectively attached to said base structure to form a second C-fold within said crotch portion, said respective distal edges being effectively unattached to said base structure within said crotch portion, each said containment flap having at least first, second, and third elastic strands spaced from each other near said distal edge of the respective containment flap such that, when said absorbent article is mounted on the body of a user, said first, second, and third elastic strands are substantially equidistant from the body of the user.

35. An absorbent article of claim 34 wherein said proximal edges of said containment flaps are spaced outwardly from said absorbent core thereby allowing for movement of the user's legs independent of any sealing between said absorbent article and the body of a user at said containment flaps.

36. An absorbent article of claim 34, said absorbent article having first and second opposing outer edges in said crotch portion, and wherein said absorbent article further comprises:

(f) a pair of longitudinally extending leg cuffs at said first and second outer edges, including leg elastics in said crotch portion of said leg cuffs, wherein said containment flaps are attached to said base structure inwardly from said leg elastics.

37. An absorbent article of claim 36, said containment flaps having a first level of tension in said crotch portion, and said leg cuffs having a second level of tension in said crotch portion, when said absorbent article is mounted to a body of a user, the first level of tension being greater than the second level of tension.

38. An absorbent article of claim 34, said base structure having first and second crotch side widths between said absorbent core and respective outer edges, in said crotch portion of said absorbent article, each said containment flap having an unfolded width greater than said respective crotch side width.

* * * * *

UNITED STATES PATENT AND TRADEMARK OFFICE
CERTIFICATE OF CORRECTION

PATENT NO. : 5,931,826
DATED : August 3, 1999
INVENTOR(S) : Michael John Faulks et al.

It is certified that error appears in the above-identified patent and that said Letters Patent is hereby corrected as shown below:

Claim 15, line 3, change "(e)" to --(a)--.
Claim 17, line 3, change "(e)" to --(a)--; line 4, after "outwardly" insert --of said--; line 5, after "respective" delete "ones of".

Signed and Sealed this

Twenty-seventh Day of March, 2001

Attest:

NICHOLAS P. GODICI

*Attesting Officer*  *Acting Director of the United States Patent and Trademark Office*